(12) United States Patent
Swisher, Jr. et al.

(10) Patent No.: US 6,446,887 B1
(45) Date of Patent: Sep. 10, 2002

(54) PORTABLE MEDICAL WASTE PLANT

(75) Inventors: George W. Swisher, Jr., Oklahoma City; Royce M. Nelson, Blanchard; Eric B. Hawkins, Yukon; Rick A. Wood, Mustang; Ronald R. Mercer, Edmond, all of OK (US)

(73) Assignee: Aegis Bio-Systems, L.L.C., Edmond, OK (US)

( * ) Notice: Subject to any disclaimer, the term of this patent is extended or adjusted under 35 U.S.C. 154(b) by 0 days.

(21) Appl. No.: 09/557,244

(22) Filed: Apr. 24, 2000

(51) Int. Cl.$^7$ .............................................. B02C 19/12
(52) U.S. Cl. .................... 241/65; 241/101.76; 241/243; 241/606
(58) Field of Search ................................ 422/307, 308, 422/309; 241/287, 295, 243, 606, 65, 101.76

(56) References Cited

U.S. PATENT DOCUMENTS

| | | | |
|---|---|---|---|
| 3,703,970 A | * 11/1972 | Benson | 241/100 |
| 4,917,310 A | * 4/1990 | Carrera | 241/243 |
| 5,186,397 A | 2/1993 | Orlando | 241/23 |
| 5,270,000 A | 12/1993 | Goldner | 422/21 |
| 5,346,142 A | * 9/1994 | Miller et al. | 241/152.2 |
| 5,364,589 A | 11/1994 | Buehler | 422/26 |
| 5,389,347 A | 2/1995 | Hall | 422/307 |
| 5,570,845 A | 11/1996 | Lewis | 241/21 |
| 5,614,157 A | 3/1997 | Hall | 422/307 |
| 5,673,861 A | 10/1997 | Miller | 241/69 |
| 5,720,438 A | * 2/1998 | Devine et al. | 241/21 |

* cited by examiner

*Primary Examiner*—Mark Rosenbaum
(74) *Attorney, Agent, or Firm*—Haynes and Boone, LLP

(57) ABSTRACT

A medical waste disposal system for loading, reducing, and sterilizing medical waste is disclosed. The system includes a frame supporting a generally sealed containment chamber, a lift assembly having a lifter mounted on a track assembly configured for generally vertical motion of the lifter. The system also includes a hopper mounted on the frame near the lift and in communication with a material feeder, a first grinder in communication with the material feeder, a first conveyor positioned to receive medical waste from the first grinder, and a second grinder in communication with the first conveyor. The system further includes a second conveyor positioned to receive waste from the second grinder, and an autoclave for thermally disinfecting the waste, mounted on the frame in the containment chamber and in communication with the second conveyor assembly. The autoclave includes a plurality of steam inlets, a waste inlet opening, and a waste outlet opening for discharging waste to a third conveyor assembly. The third conveyor assembly is positioned to receive waste from the autoclave and to convey the waste to a disposal container. The system further includes a steam generation plant mounted on the frame in the containment chamber and in communication with the steam inlets of the autoclave.

15 Claims, 12 Drawing Sheets

PORTABLE MEDICAL WASTE PLANT

FIELD OF THE INVENTION

The present invention relates generally to the field of waste disposal. It relates particularly to a portable medical waste treatment of medical waste prior to disposal.

BACKGROUND OF THE INVENTION

Disposable medical items such as gowns, gloves, and surgical instruments such as syringes and scalpels are utilized in the normal course of business of hospitals. After these disposable medical items are used they are waste, and are often contaminated with microorganisms of infectious diseases. The disposal of such infected material waste, sometimes including pathological tissue, has been a problem in that such waste must be sterilized before it can be disposed of.

In the past, individual hospitals and medical centers have been provided with sterilization systems, such as autoclaves or incinerators, for sterilizing the medical waste. The medical waste can then be shredded and loaded into a disposal container for disposal in a landfill. Thus, each hospital or medical institution must have its own sterilizing unit, and the medical waste must be loaded and unloaded for each transfer between hospital and sterilizer unit, sterilizer unit and shredding facility, and shredding facility and landfill from the sterilizer unit, the shredding facility, and the landfill. Should the medical waste at the medical institution not be sterilized before pick-up, the hauler must deliver the waste to an incinerator or other sterilizing plant to dispose of the medical waste.

It would be advantageous to provide for a portable medical waste disposal system which picks up contaminated medical waste from the medical institution, shreds and sterilizes the medical waste, and then loads the shredded medical waste into a disposal container.

SUMMARY OF THE INVENTION

An exemplary embodiment of the present invention pertains to a medical waste disposal system for loading, reducing, and sterilizing medical waste. The system includes a frame supporting a plurality of contiguous sidewalls and top walls to form a generally sealed containment chamber, at least one lift assembly having a lifter mounted to the frame on a track assembly, wherein the track assembly is configured for generally vertical motion of the lifter. The system also includes a hopper assembly mounted on the frame in the containment chamber near the lift assembly and in communication with a delta, or material, feeder, a first grinder in communication with the material feeder and generally disposed below the material feeder and the hopper assembly, a first conveyor assembly positioned to receive medical waste from the first grinder, and a second grinder in communication with the first conveyor assembly. The system further includes a second conveyor assembly positioned to receive medical waste from the second grinder, and an autoclave, mounted on the frame in the containment chamber and in communication with the second conveyor assembly. The autoclave includes a plurality of steam inlets, a waste inlet opening, and a waste outlet opening for discharging medical waste to a third conveyor assembly. The third conveyor assembly is positioned to receive medical waste from the autoclave and to convey the medical waste to a disposal container. The system further includes a steam generation plant mounted on the frame in the containment chamber and in communication with the steam inlets of the autoclave.

Another embodiment of the present invention pertains to a grinder disposed in a path of medical waste in a medical waste disposal plant. The grinder includes a grinding housing having opposed, parallel sides defining a grinding chamber with the grinding housing having an inlet and an outlet in communication with the grinding chamber and the path of medical waste. The grinder also includes a cutter assembly disposed in the grinding chamber, the cutter assembly including a shaft rotatably mounted to the sides of the grinding housing and connected to a means for rotation, a plurality of first cutter blades mounted on the shaft at axially spaced apart intervals and extending radially beyond a plurality of second cutter blades mounted on the shaft at spaced apart intervals between said first cutter blades. The grinder further includes a movable finger plate rotatably mounted to the sides of the grinding housing in the grinding chamber and positioned to allow the first and second cutter blades to move between a plurality of slots in the finger plate. The finger plate is connected to a means for movement toward and away from the first and second cutter blades and a transducer responsive to selected forces on the finger plate.

Another embodiment of the present invention pertains to a medical waste disposal system for loading, reducing, and sterilizing medical waste. The system includes a means for transporting the medical waste disposal system, a means for loading medical waste into the medical waste disposal system, and a means for grinding medical waste into a reduced volume of medical waste in communication with the means for loading. The system also includes a means for sterilizing medical waste in the medical waste disposal system, and a means for conveying medical waste through the medical waste disposal system between the means for grinding and the means for sterilizing.

DETAILED DESCRIPTION OF THE PREFERRED EMBODIMENTS

Figure 1:
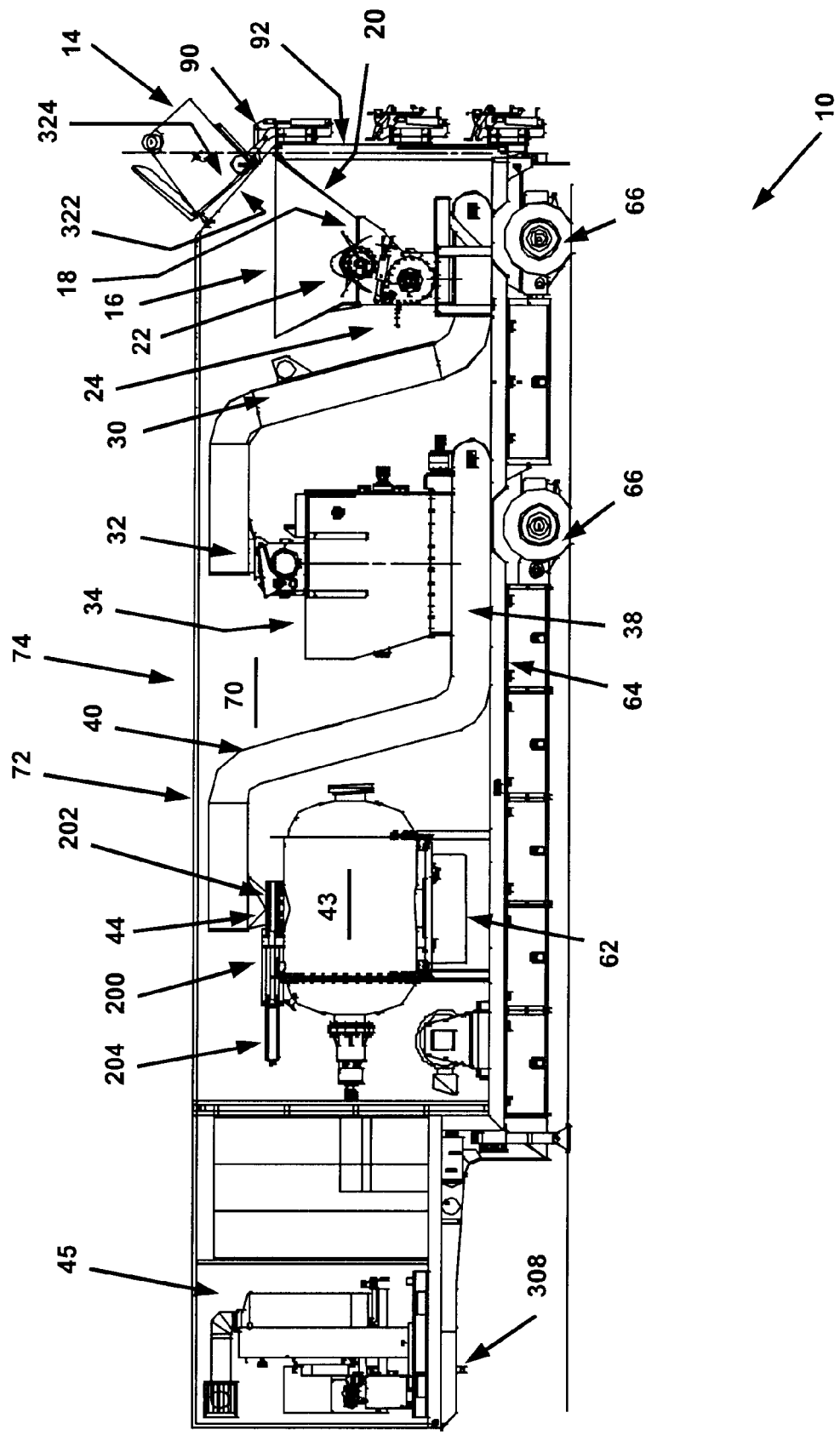
FIG. 1 is a side elevation of an exemplary embodiment of a portable medical waste treatment plant.
Figure 2:
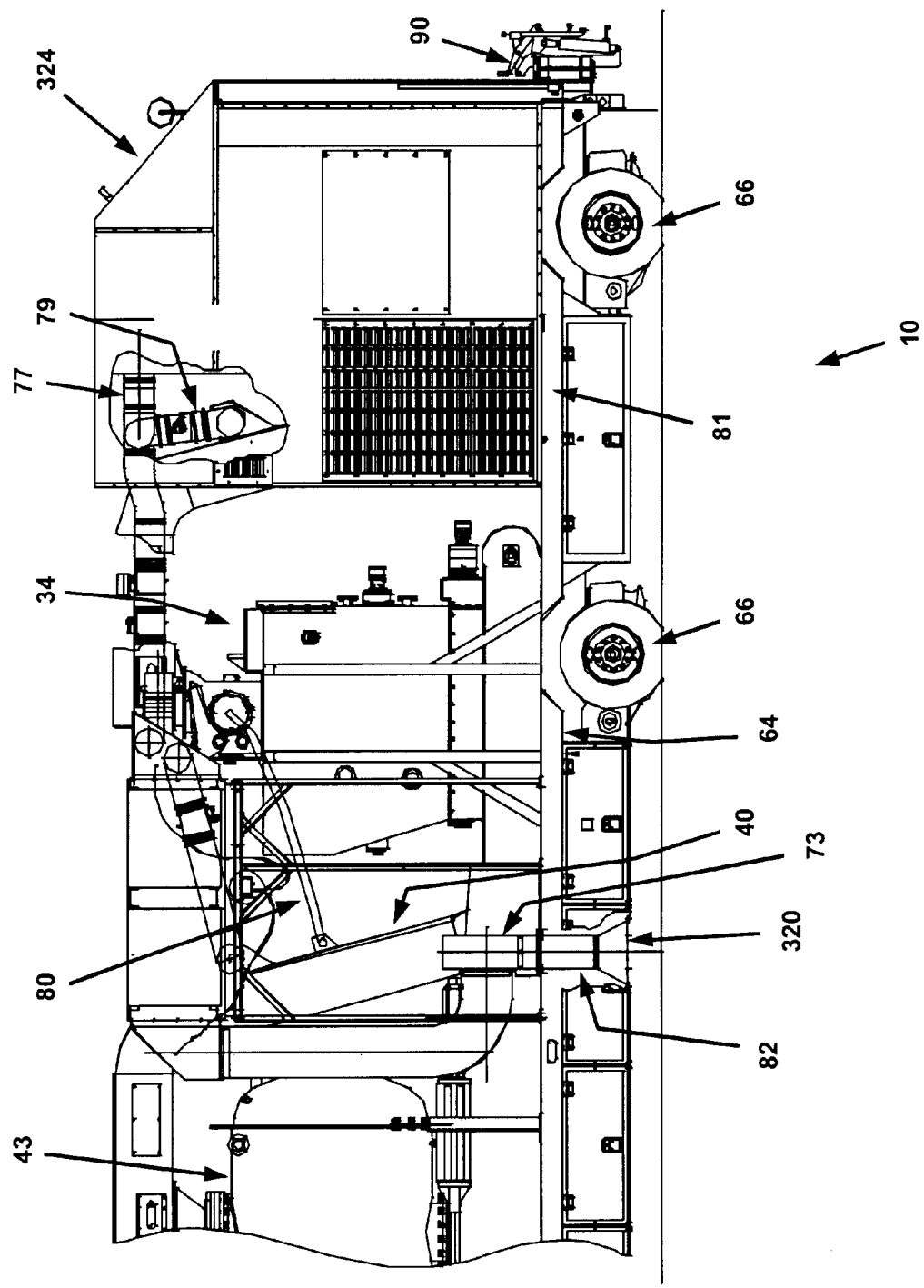
FIG. 2 is a fragmentary side elevation of the portable medical waste treatment plant shown in FIG. 1 and having a containment cover removed.

FIG. 1 shows a medical waste disposal system 10. Medical waste disposal system 10 includes a lift assembly 12 for lifting waste containers 14 filled with contaminated waste material, and dumping the waste into a hopper assembly, or hopper, 16. The contaminated waste material may be, e.g., medical waste material received from a hospital. Hopper 16 has an upwardly disposed material inlet opening 324 and an outlet opening 18 formed in a lower end 20 of hopper 16. A delta feeder, or material feeder, 22 communicates with opening 18 to receive the contaminated waste material and put it into a first grinding assembly, or grinder, 24. Material feeder 22 is termed a delta feeder because of the triangular, or delta-shaped, cross section of its impeller 330. Material feeder 22 is provided with a plurality of paddles 328 connected to a shaft 326 rotated by a motor 336 (shown in FIG. 6) which moves the contaminated waste material disposed in hopper 16 to first grinder 24, which is disposed generally below material feeder 22 and hopper 16.

First grinder 24 receives contaminated waste material from material feeder 22. First grinder 24 reduces, grinds, or shreds the contaminated waste material generally into a uniformly coarse particle size. The terms "reduce", "grind," and "shred" are used interchangeably herein. The coarsely shredded contaminated waste material is then discharged from an outlet 28 of first grinder 24. A first conveyor assembly 30 receives the coarsely shredded contaminated waste material from outlet 28 and conveys it to an inlet 32 of a second grinder assembly, or second grinder, 34.

Second grinder 34 receives the coarsely shredded contaminated waste material and further reduces the particle size of the contaminated waste material to a generally uniform and smaller size. Typically, a particle of waste material leaving second grinder 34 has a maximum dimension of less than one inch and is generally not recognizable or identifiable as to its source; i.e., its original form or purpose.

The reduced contaminated waste material is then discharged from an outlet 36 of second grinder 34 to be received by an inlet 38 of a second conveyor assembly 40. First and second conveyor assemblies 30 and 40 are, in the exemplary embodiment, of the belt type of conveyor. In an alternative embodiment (not shown), first and second conveyor assemblies 30 and 40 are of the screw conveyor type including a rotatable helical augur coaxially disposed within an outer tubular casing.

The reduced contaminated waste material is then conveyed by second conveyor 40 into an autoclave 43, through an inlet opening 44 of autoclave 43, where the shredded waste material is sterilized by steam introduced into autoclave 43 from a steam generation plant 45. In an exemplary embodiment, autoclave 43 is a pressure vessel of 115 cubic feet internal volume and is provided with a jacketed, or thermally insulated, wall and a hydraulic motor drive of an auger 332 (described below). The steam generator plant 45 may be mounted on the frame 64 or may be external to the medical waste disposal system 10, such as a hospital steam plant.

Inlet opening 44 of autoclave 43 is closed and sealed (as described below) when the reduced contaminated waste material has been loaded therein. Autoclave 43 is then filled with steam at 250 degrees F. and 1 atmosphere, or approximately 15 psig, of gauge pressure.

Figure 11:
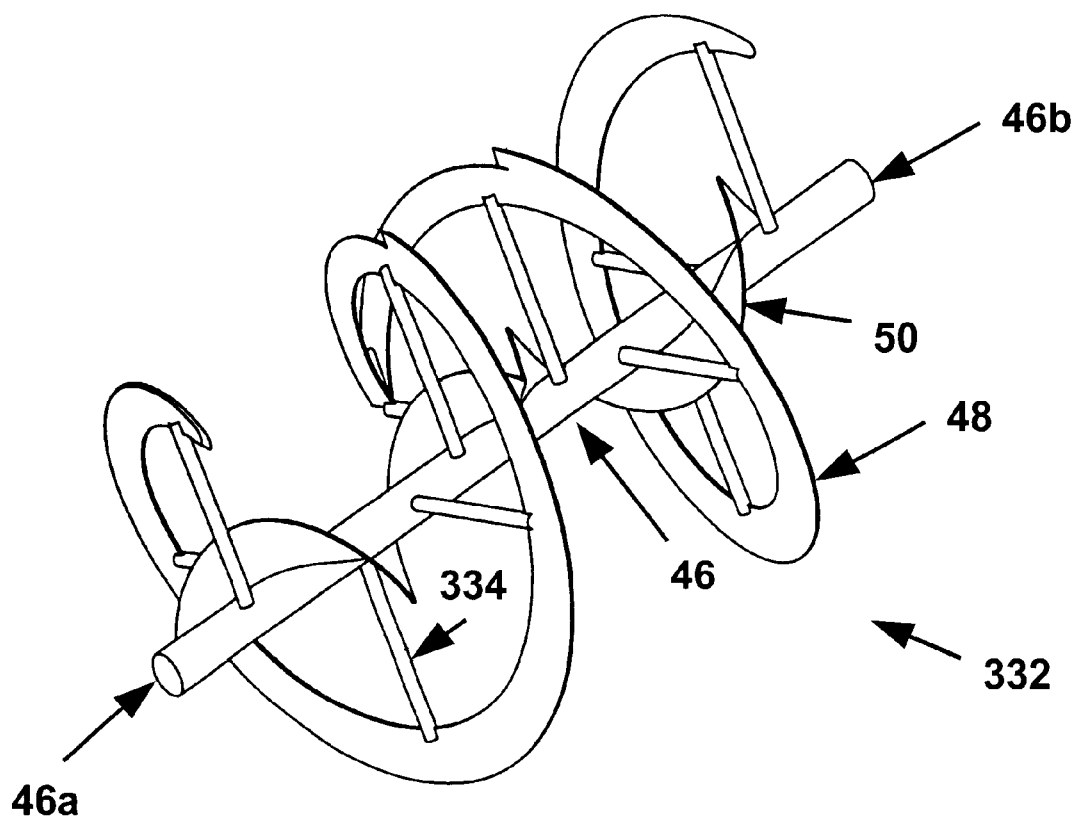
FIG. 11 is a perspective view of an auger within the autoclave shown in FIG. 10.

Autoclave 43 includes an auger assembly 332, which comprises a shaft 46, a first helical auger 48, and a second helical auger 50. As shown in FIG. 11, first auger 48 may be supported upon shaft 46 by a series of rigid spokes 334, and auger 50 may be supported upon shaft 46 by a conventional means of securing: e.g., welding. Augers 48 and 50 each have a first portion and a second portion of approximately equal lengths and of opposite helix angles forming screw blades having opposed pitches. Auger 48 is provided an outside diameter and an inside diameter, and auger 50 is provided an outside diameter which is substantially smaller than the inside diameter of auger 48. Both auger 50 and auger 48 are secured to shaft 46, these three elements sharing a common axial center line, and auger 48 therefore peripherally surrounds auger 50. The portion of auger 48 having a negative helix angle surrounds the portion of auger 50 having a positive helix angle, and the portion of auger 48 having a positive helix angle surrounds the portion of auger 50 having a negative helix angle. Rotation of auger assembly 332 about the longitudinal axis of shaft 46 therefore causes augers 48 and 50 to function as screw conveyors, with one of augers 48 and 50 conveying material from a longitudinal center of autoclave 43 toward first and second ends 54, 56 of autoclave 43, while the other of augers 48, 50 is simultaneously conveying material back toward the longitudinal center of autoclave 43. The reduced, contaminated waste material particles within autoclave 43 are therefore constantly being tumbled and agitated, exposing all surfaces of each particle to the steam within autoclave 43, insuring that the waste material is uniformly sterilized by the steam.

The reduced waste material is thus tumbled and heated for a length of time sufficient to sterilize the waste material. In an exemplary embodiment, lengths of time of autoclaving, of, typically and approximately, twenty to thirty minutes have been sufficient to ensure substantially complete sterilization of the waste material. Longer and shorter lengths of time are easily provided for as are other temperatures and pressures of the steam, by programming of a programmable logic controller (PLC, not shown) in software or hardware. Similarly, the PLC may be used to energize selected valve actuators to route steam to various locations with containment chamber 74 for disinfecting equipment or surfaces at those locations; e.g., first and second conveyors 30, 40; first and second grinders 24, 34, etc.

Figure 10:
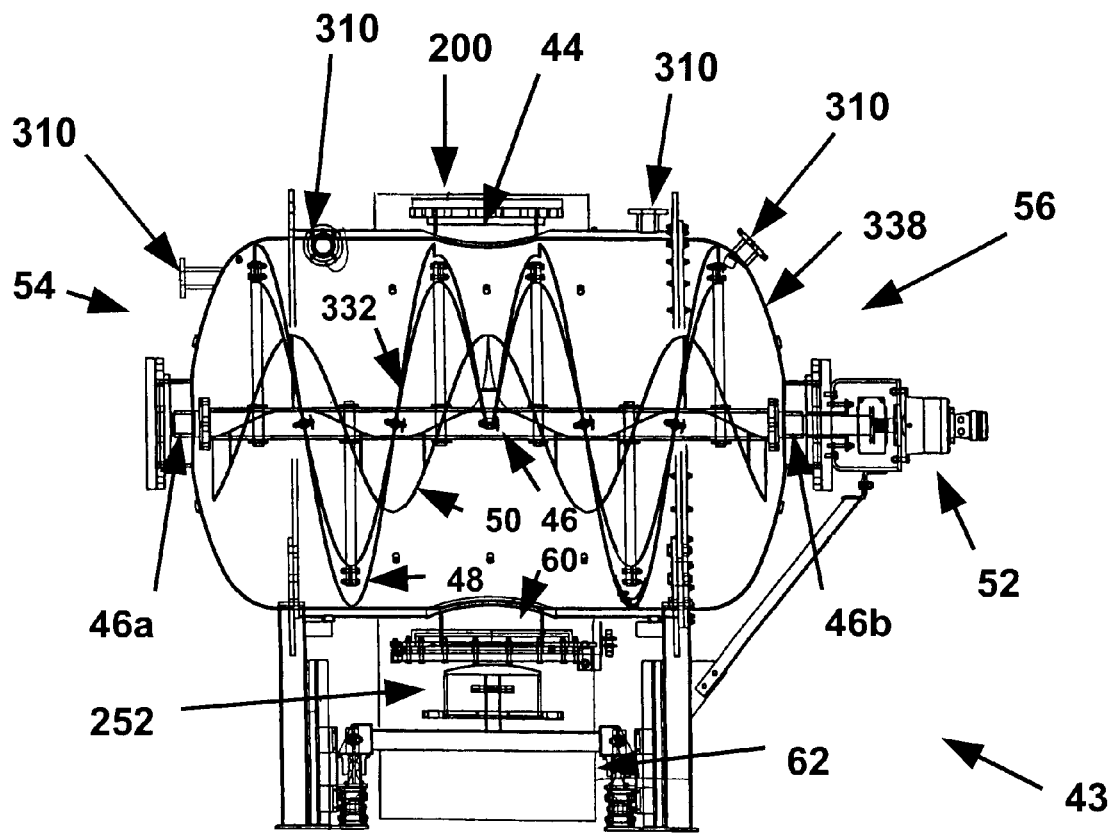
FIG. 10 is a side elevation of an autoclave of an examplary portable medical waste treatment plant.
Figure 12:
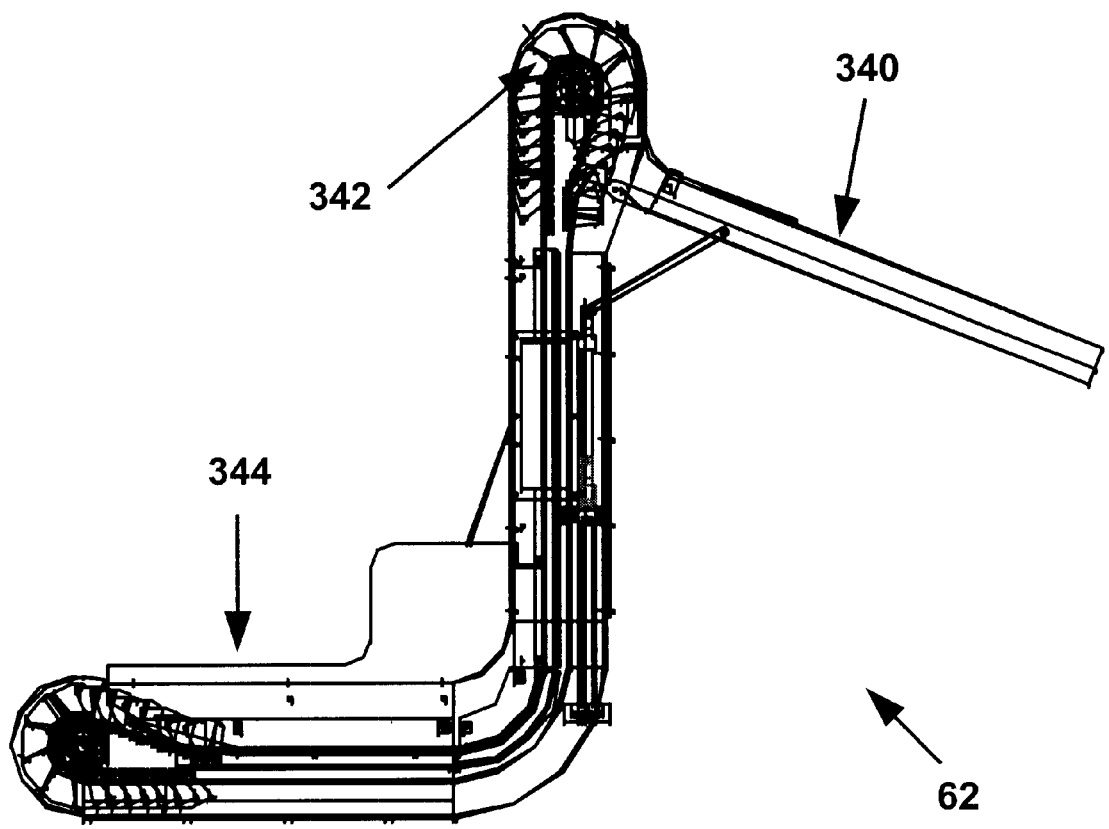
FIG. 12 is a rear elevation of a discharge conveyor of the portable medical waste treatment plant shown in FIG. 1.

The sterilized waste material is then discharged through an outlet opening 60 of autoclave 43 onto a third conveyor assembly 62 (shown in FIGS. 1, 10, and 12). Third conveyor assembly 62 conveys the sterilized, reduced waste material to a waste material bin, hopper, or container (e.g., a dumpster) positioned outside a containment chamber 74 (described below) for transportation to a landfill.

As best shown in FIG. 1, all of the equipment herein described of medical waste disposal system 10 is mounted upon a frame 64 which is supported by wheels 66 and includes a trailer hitch (e.g., a fifth wheel pintle 308 in the nature of a large commercial trailer) in order that medical waste disposal system 10 can be moved from site to site. Thus, medical waste disposal system 10 provides for a portable and efficient method for loading, reducing, and sterilizing contaminated material such as medical waste. Wheels 66 and pintle 308 may be eliminated or removed, if desired, and medical waste disposal system 10 used as a pre-packaged, skid-mounted facility. It should also be noted that first and second grinders 24, 34 are configured to reduce all types of medical waste material, including, but not limited to, paper and fabric bandages and gowns, glass and plastic syringes, metal needles and scalpels, and pathological tissue, without separation, before entering into medical waste disposal system 10.

Medical waste disposal system 10 is provided with a plurality of contiguously disposed sidewalls 70 and a top wall 72 configured to form a generally sealed containment chamber 74 into which material feeder 22, first grinder 24, first conveyor assembly 30, second grinder assembly 34, second conveyor assembly 40, autoclave 43, steam generation plant 45, and third conveyor assembly 62 are disposed. Hopper 16, requiring a large opening into which the medical waste is dumped, is not contained within containment chamber 74.

Medical waste disposal system 10 further includes a filter and air exhaust system 76 having a first inlet air duct 77 communicating with hopper 16, a second inlet air duct 78 (not shown) disposed in containment chamber 74, a third inlet air duct 79 communicating with the first conveyor assembly 30, a fourth inlet air duct 80 communicating with second conveyor assembly 40, and an exit air duct 82 for discharging air through a floor of containment chamber 74. Filter and air exhaust system 76 includes a fan 73 for drawing air through ducts 77, 78, 79 and 80 and forcing the air through a filter assembly 81. Filter assembly 81 may include several layers of filtering media (e.g., metal or glass fiber, mesh reinforcement, activated charcoal, biocide-impregnated material, HEPA, etc.). Fan 73 discharges the air through exit duct 82 and an air outlet 320 located in a lower surface of containment chamber 74. Filter and air exhaust system 76 slightly lowers atmospheric pressure within containment chamber 74, thereby maintaining a positive air flow into containment chamber 74 through any openings or leaks which may exist in one or more surfaces of containment chamber 74, as well as through hopper 16 while waste material is being dumped from disposal containers 14.

Steam conduits and valves (not shown) within containment chambers 74 are configured and disposed to selectively deliver steam from steam generating plants 45 to first and second grinders 24, 34 and first and second conveyors 30, 40 to sterilize these components before, during and after operation in order to preclude adverse microbial growth.

Figure 3:
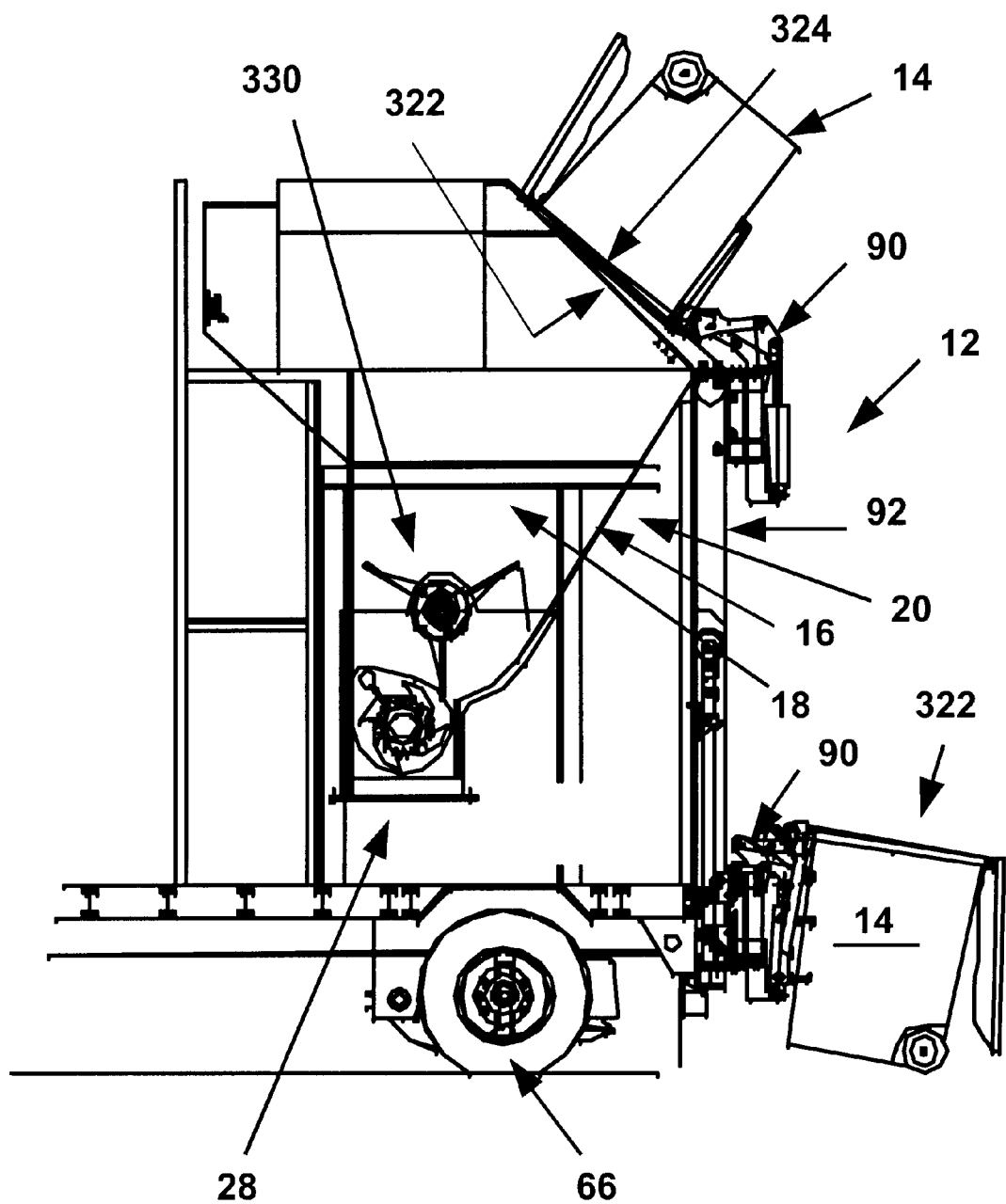
FIG. 3 is a side elevation of the portable medical waste treatment plant shown in FIG. 1 and showing a loading and feeding apparatus.
Figure 4:
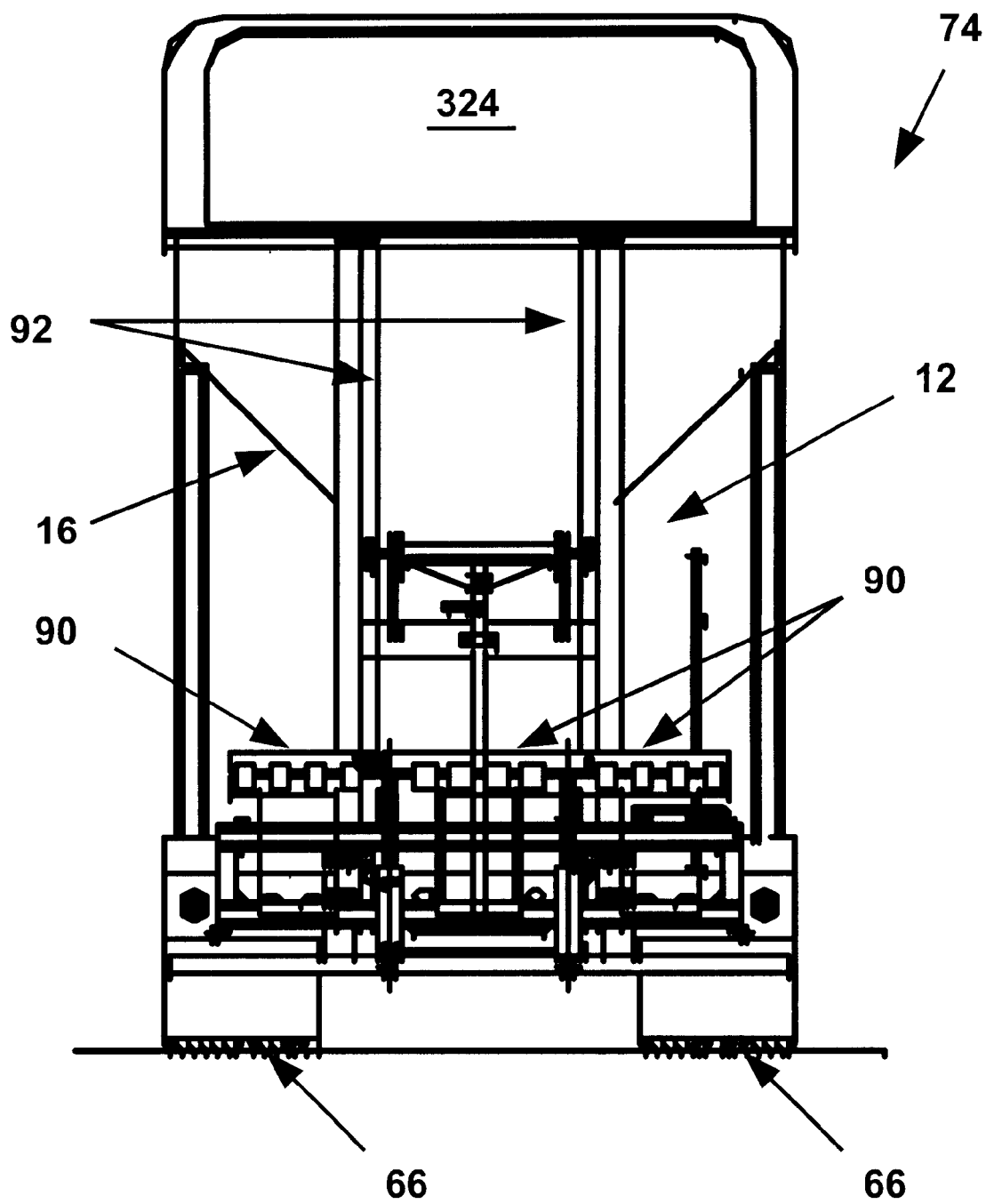
FIG. 4 is a rear elevation of the portable medical waste treatment plant shown in FIG. 1.

Lift assembly 12 is best shown FIGS. 1, 3, and 4. Lift assembly 12 includes a generally vertically disposed track 92 positioned in the region of a rear surface of frame 64, and a lifter 90 for lifting at least one disposal container 14 to a waste inlet 324 of hopper 16. In the illustrated instance, lifter 90 is configured to hold and lift up to three disposal containers 14 simultaneously. Lifter 90 lifts the at least one disposal container 14, having an open top 322 disposed upwardly, to the top of track 92, whereupon it tilts and partially inverts disposal container 14 so that contaminated waste material pours from disposal container 14 through opening 322 and opening 324 into hopper 16. Simultaneously, fan 73 is used to draw air through hopper 16 so that any light weight contaminated material (e.g., fabric or paper) will not escape but will be drawn into hopper 16.

Portable medical waste plant 10 may further include a radiation sensor (not shown) which is preferably disposed in the region of hopper inlet opening 324 for measuring the level of radioactivity of incoming contaminated waste material. The radiation sensor may be in communication with the PLC, and either or both of the radiation sensor and the PLC may be provided a visual and/or audible alarm configured to trip when the level of radiation exceeds a predetermined level.

Upon disposal container 14 having been emptied, it is disinfected with a spray of disinfecting fluid from a spray system (not shown) of medical waste disposal system 10. Lifter 90 is then lowered to return disposal container 14 to the pavement or other surface from which it was picked up.

In an exemplary embodiment, container lifter 90 includes a strain gauge to provide an output signal of the weight lifted by lifter 90. The difference in weights when being lifted filled with contaminated waste material and being lowered empty can be used as a basis for billing the medical institution or other purchaser of the waste decontaminating service provided by medical waste disposal system 10.

Figure 5:
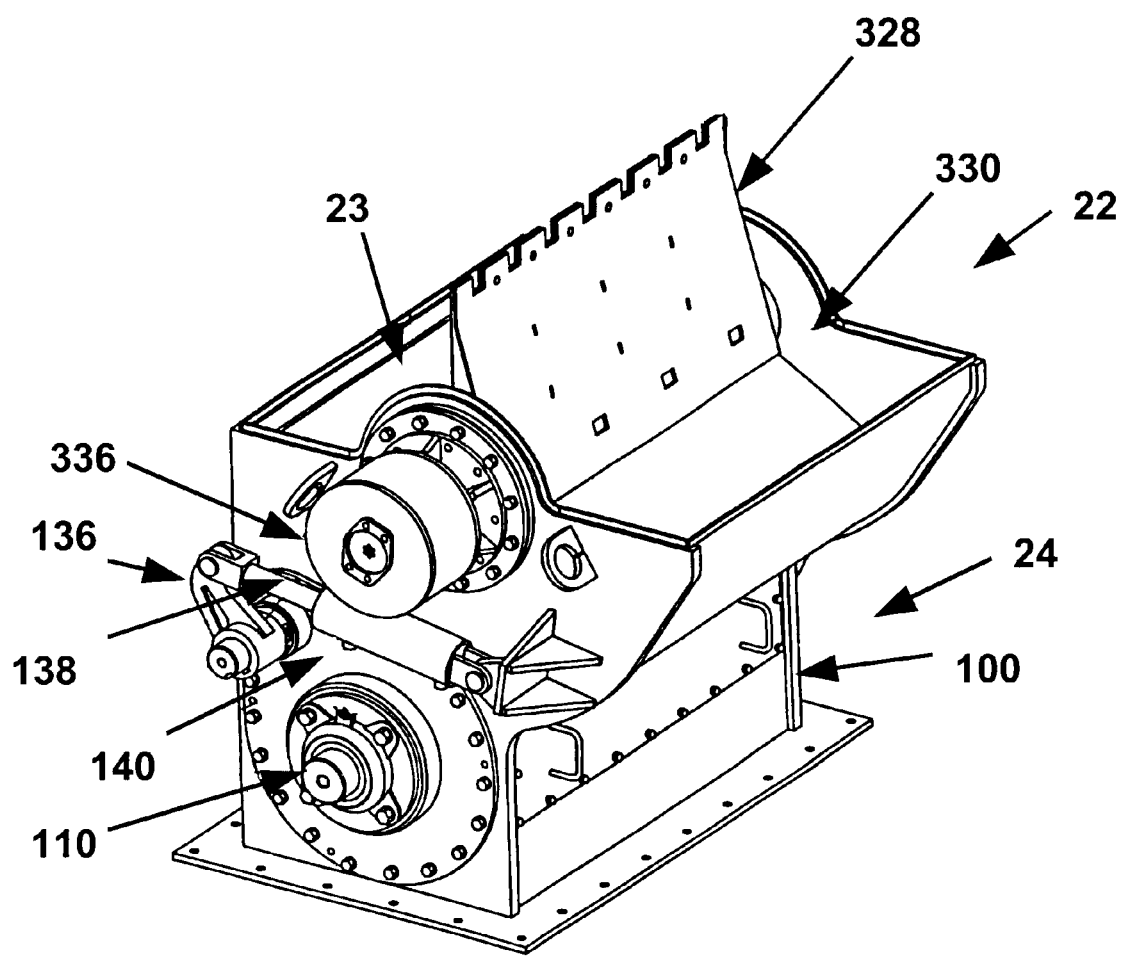
FIG. 5 is a perspective view of a first grinder and material feeder assembly of an examplary portable medical waste treatment plant.
Figure 6:
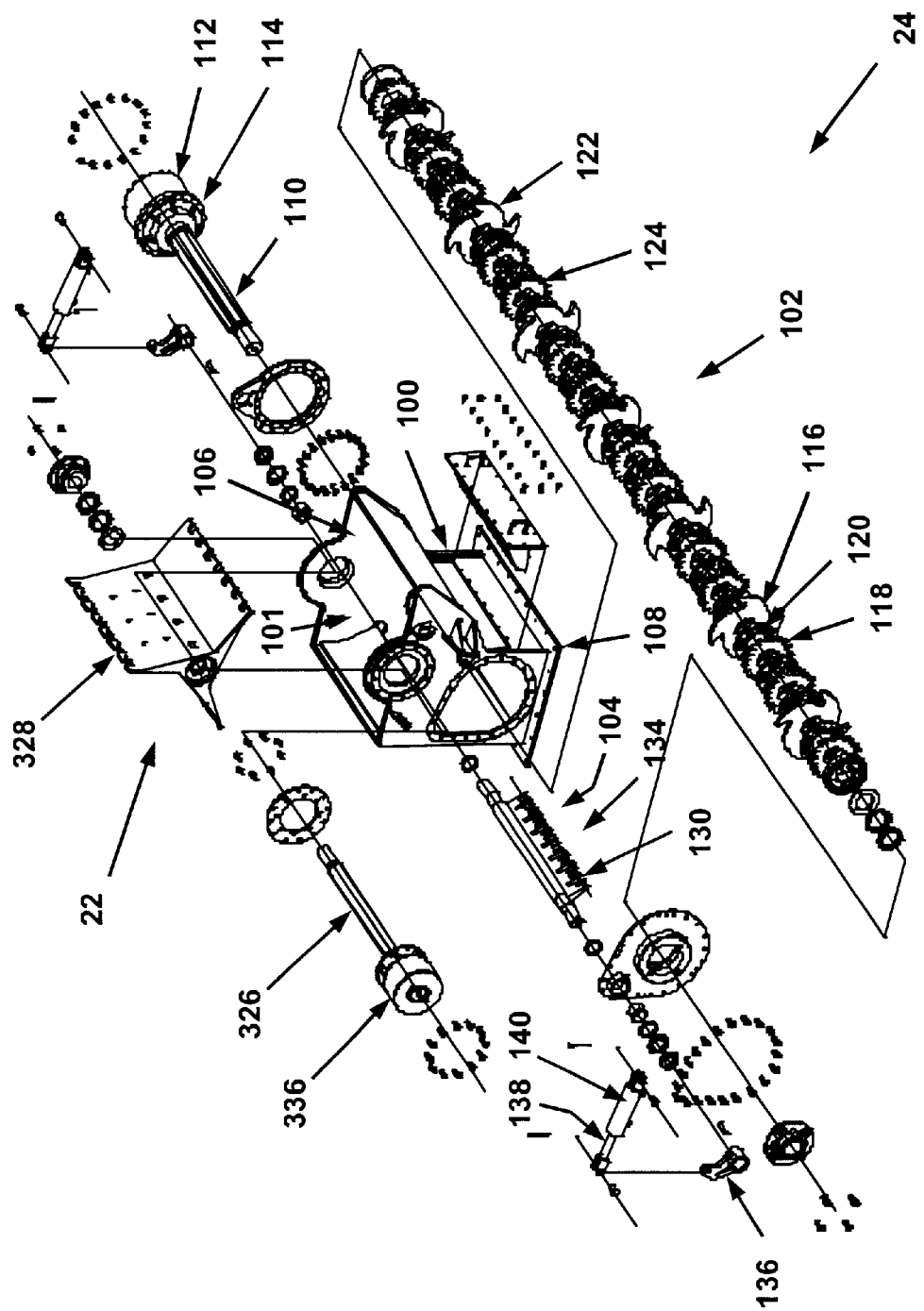
FIG. 6 is an exploded perspective view of the first grinder and material feeder assembly shown in FIG. 5.

FIGS. 5 and 6 illustrate first grinder 24 and material feeder 22. First grinder 24 includes a grinding housing 100 defining a grinding chamber 101, a cutter assembly 102 disposed within grinding chamber 101, and a movable finger plate 104 disposed within grinding chamber 101 and adjacent cutter assembly 102. Material feeder 22 is disposed within an upper inlet opening 23 of housing 100, and includes three paddles 328 of an impeller assembly 330 (described below).

Grinding housing 100 is provided with a first grinder inlet 106 disposed within housing 100 and immediately below material feeder 22 and above cutter assembly 102 for receiving waste material from material feeder 22. Grinding housing 100 also includes an outlet 108 disposed generally below cutter assembly 102 for discharging the coarsely reduced contaminated waste to a first conveyer assembly 30.

Feeder 22 includes an impeller assembly 330, which is provided with at least three paddles 328 secured to a shaft 326. A power source, shown as a shaft-mounted hydraulic motor 336, rotates shaft 326 and paddles 328 within the upper portion of housing 100 to feed waste material to first grinder 24. It should be understood that an electric motor or an internal combustion motor is also contemplated for use in rotating the shaft 326.

Cutter assembly 102 includes a shaft 110 transversely disposed through grinding chamber 101 and rotatably mounted to opposing, parallel sides of grinding housing 100. Shaft 110 is rotated by a power source, shown as a shaft-mounted hydraulic motor 112 provided with a transmission 114 in a motor and transmission assembly. In the exemplary embodiment, motor 112 and transmission 114 are configured to be selectively operable at various speeds. A plurality of first cutter blades 116 and second cutter blades 118 are mounted to shaft 110 at predetermined intervals along the length of shaft 110. Spaces 120 are disposed between first cutter blades 116 and second cutter blades 118 to space the blades apart.

First cutter blades 116 and second cutter blades 118 are generally disc-like in shape, with teeth on their peripheries. First cutter blades 116 are larger in outside diameter than are second cutter blades 118. First cutter blades 116 are spaced apart and provided with large teeth 122 (in the illustrated instance, four in number per blade) which are adapted to grip the waste material when the waste material is disposed through inlet 106 and to thereby draw the waste material into the path of second cutter blades 118. Second cutter blades 118 are provided with teeth 124 which are smaller than the teeth 122 of first cutter blades 116. Second cutter blades 118 function to cut, fracture, or grind the waste material into a coarse particle size as the waste material is passed through first grinder 24.

Movable finger plate 104 is pivotally mounted to opposed parallel sides of grinding housing 100 and is positioned in the cutting path of first cutter blades 116 and second cutter blades 118. Movable finger plate 104 is provided with a plurality of spaced-apart slots 130 disposed in preselected positions along a first side 134 of finger plate 104. Each slot 130 receives first cutting blades 116 or second cutting blades 118. Movable finger plate 104 is provided a yoke 136 rigidly affixed to one end of finger plate 104. Yoke 136 is pivotally connected to a rod 138 of a fluid cylinder 140. Fluid cylinder 140 is pivotally mounted at its cap end and is pressurized (in the illustrated instance, to approximately 2000 psig) to resist rotating movement of movable finger plate 104. The fluid cylinder 140 is preferably a hydraulic cylinder and piston assembly, but it is contemplated that a pneumatic cylinder assembly may also be used.

In operation, motor 112 is actuated to start rotation of transmission 114 and of shaft 110 and thus of first cutter blades 116 and second cutter blades 118. The waste material, such as medical waste disposed in plastic trash bags, is fed through material feeder 22 and into inlet 106 of grinding chamber 101, where the waste material contacts first cutter blades 116. First cutter blades 116 grip the waste material and force it against movable finger plate 104, where the waste material is reduced to particles of a coarse size by first cutter blades 116 and second cutter blades 118. The coarsely reduced waste material then exits from grinding chamber 101 through outlet 108 to be received by first conveyor 30.

The rotatable mounting of finger plate 104 in grinding chamber 101 and the pivotally flexible mounting of yoke 136 of finger plate 104 to rod 138 of fluid cylinder 140 permit finger plate 104 to selectively rotate away from cutter blades 116, 118 when a predetermined amount of force is applied to finger plate 104. Binding is therefore prevented when an excess amount of material is disposed between cutter blades 116, 118 and finger plate 104. When the force is removed from finger plate 104, fluid cylinder 140 forces finger plate 104 back to its earlier position so that the reducing in size of the waste material automatically continues. A controller (e.g., a programmable logic controller or PLC) can be adapted to control fluid cylinder 140 to permit an operator of medical waste disposal system 10 to selectively rotate finger plate 104 away from and toward first and second blades 116, 118.

Figure 7:
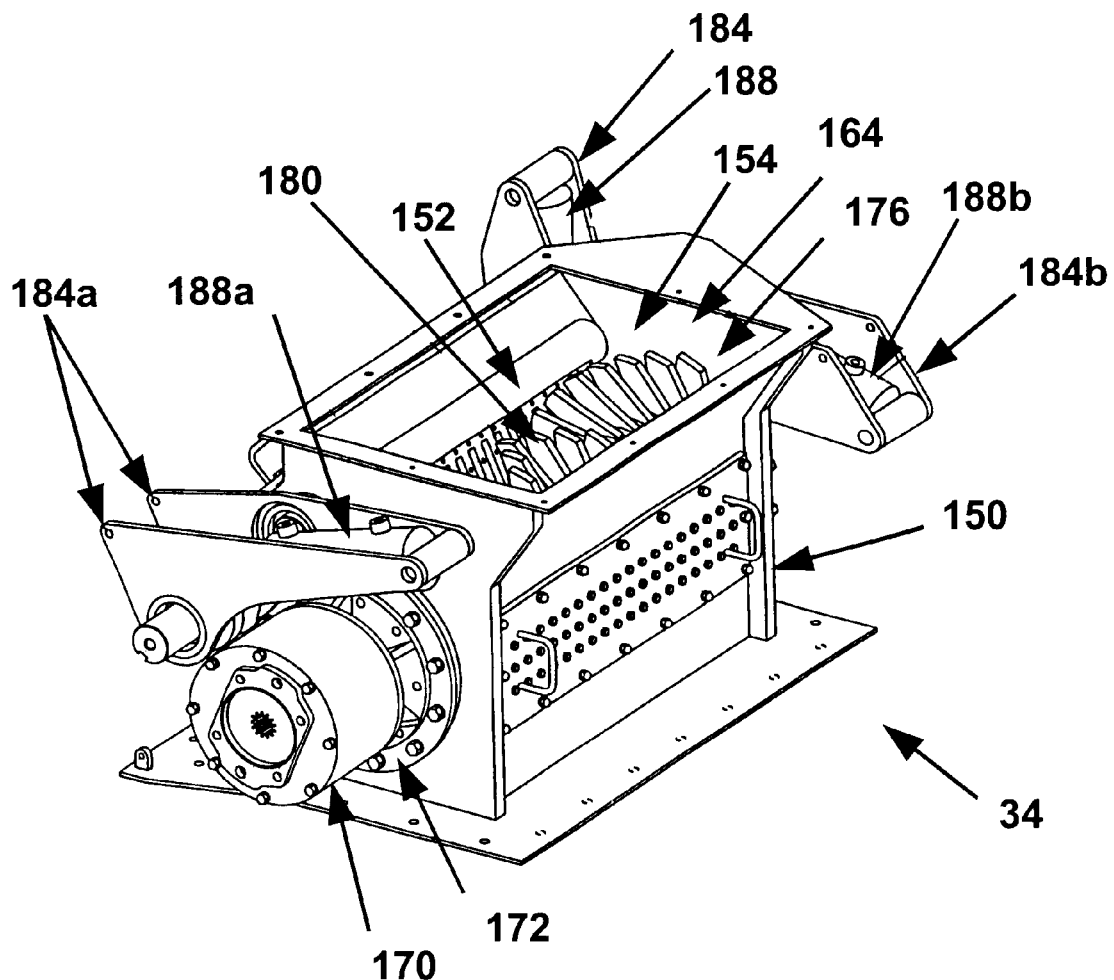
FIG. 7 is a perspective view of a second grinder of an examplary portable medical waste treatment plant.
Figure 8:
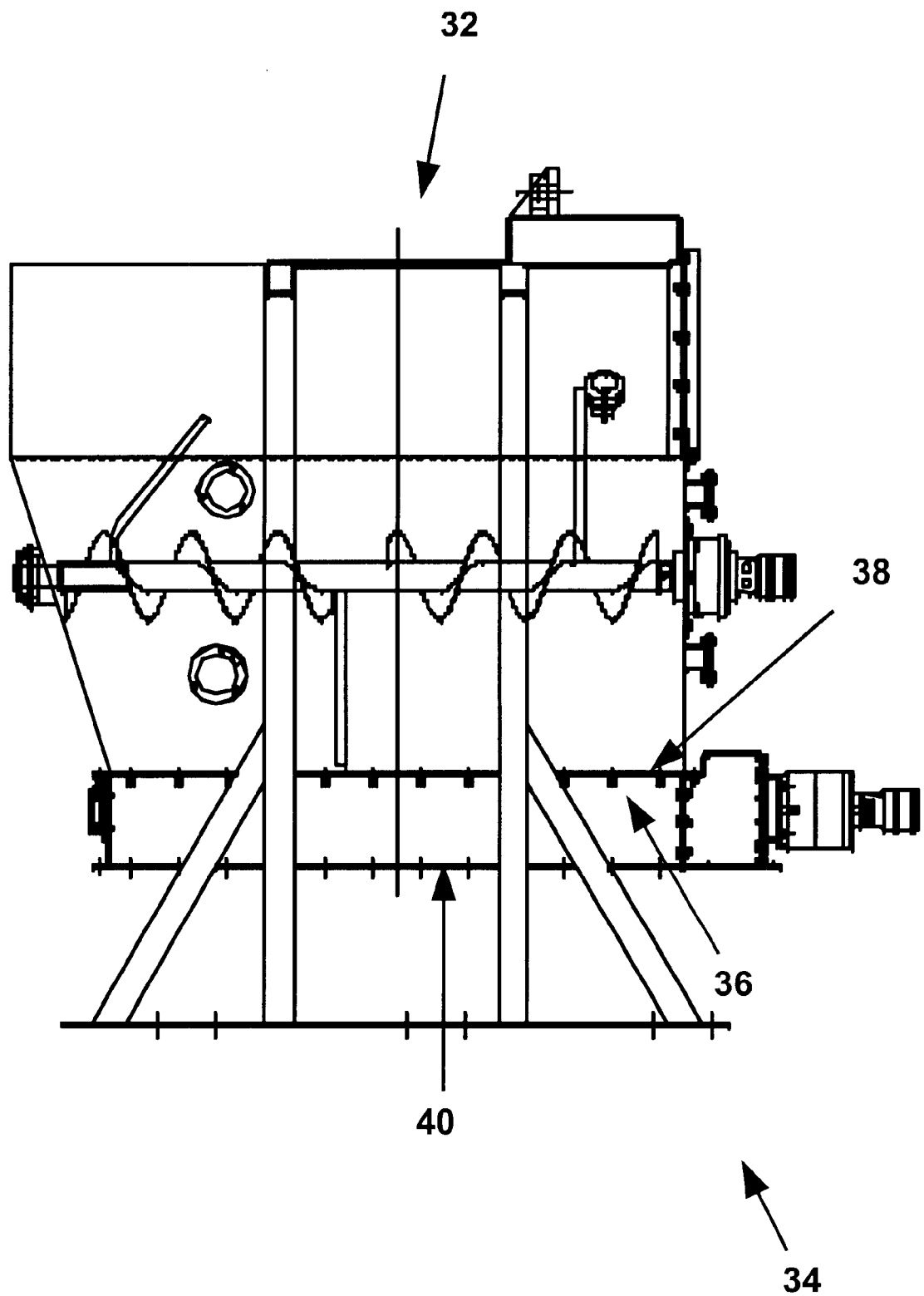
FIG. 8 is a side elevation view of the second grinder shown in FIG. 7.
Figure 9:
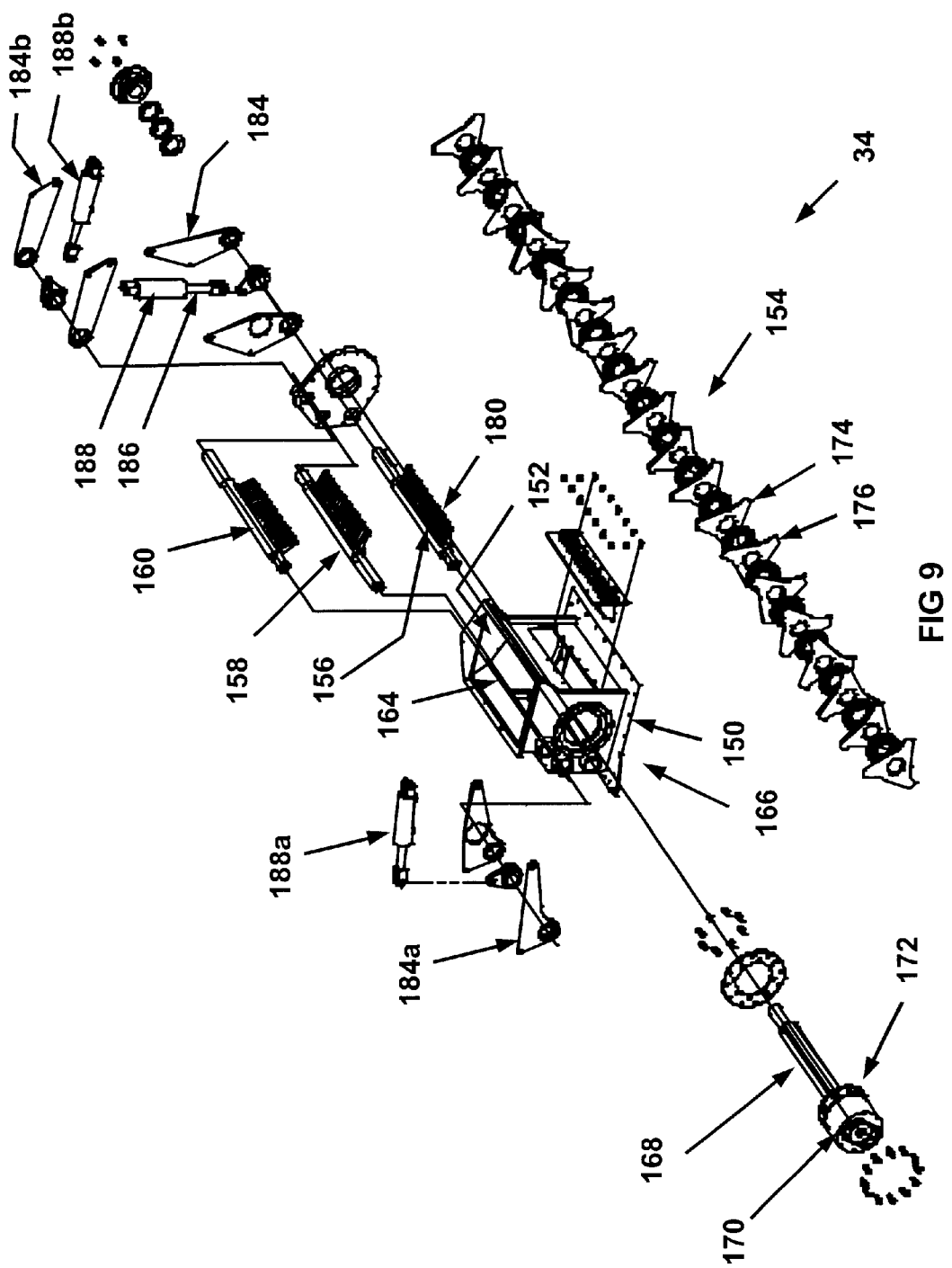
FIG. 9 is an exploded perspective view of the second grinder shown in FIG. 7.

Second grinder 34 is shown in detail in FIGS. 7 through 9. Second grinder 34 includes a grinding housing 150 defining a grinding chamber 152, a cutter assembly 154 disposed within grinding chamber 152, and a plurality of movable finger plates 156, 158, and 160 disposed in grinding chamber 152 and positioned in the cutting path of cutter assembly 154.

Grinding housing 150 is provided with an inlet 164 disposed generally above cutter assembly 154 for receiving waste material from first conveyor 30, and an outlet 166 disposed generally below cutter assembly 154 for discharging the reduced waste material to a second conveyor assembly 40.

Cutter assembly 154 includes a shaft 168 transversely disposed through grinding chamber 152 and rotatably mounted to opposed, parallel sides of grinding housing 150. Shaft 168 is rotated by a power source, shown as a shaft-mounted hydraulic motor 170 provided with a transmission 172 in a motor and transmission assembly. In the exemplary embodiment, motor 170 and transmission 172 are configured to be selectively operable at various speeds.

A plurality of spaced-apart cutter blades 174 is mounted in preselected positions along shaft 168. Each cutter blade 174 has teeth 176 formed on the periphery thereof. Adjacent cutter blades 174 are rotationally offset from each other by approximately 4.9° when they are installed upon shaft 168. This rotational staggering of teeth 176 of adjacently disposed cutter blades 174 provides cutter assembly 154 with a substantially constant pressure on finger plates 156, 15, and 160 when second grinder 34 is reducing the waste material.

Movable finger plates 156, 158, and 160 are spatially disposed about at least a portion of the cutting path of cutter blades 174. Movable finger plates 156, 158, and 160 are generally similar in construction and function, excepting that a portion of finger plate 158 extends from an opposite side of housing 150 than do finger plates 156 and 160. Thus, only finger plate 156 will be described below and it is to be understood that this description will apply equally to finger plates 158 and 160.

Movable finger plate 156 is rotatably mounted to opposed parallel sides of housing 150. Finger plate 156 is provided with a plurality of spaced apart, uniformly sized slots 180 disposed in preselected positions along a first side 182 of finger plate 156. Each slot 180 is adapted to receive at least a portion of one of the cutting blades 174. Movable finger plate 156 is provided a yoke 185 rigidly affixed to one end thereof. Yoke 184 is pivotally connected to a rod 186 of a fluid cylinder 188. The cap end of fluid cylinder 188 is pivotally mounted to supporting structure (not shown) and pressurized (in the illustrated instance, to approximately 400 psig) to resist rotating movement of finger plate 156.

In operation, motor 170 with transmission 172 is started to begin the rotation of shaft 168 and thus of cutter blades 174. Coarsely reduced waste material is fed from first conveyor 30 into grinding chamber 152 so that the waste material contacts cutter blades 174. Cutter blades 174 grip the partially reduced waste material and force it sequentially against each finger plate 156, 158, and 160, where the waste material is further reduced in size by cutter blades 174. The reduced waste material then exits grinding chamber 152 through outlet 166 to be received by second conveyor 40.

The rotatable mounting of finger plates 156, 158, and 160 to grinding housing 150 and the pivotal mounting of yokes 184, 184a, and 184b, respectively, of the finger plates to the rods of hydraulic cylinders 188, 188a, and 188b, respectively, permit finger plates 156, 158, and 160 to selectively rotate away from cutter blades 174 when force in excess of a predetermined amount is applied to the respective finger plates. Binding is thereby prevented when an excessive amount of material is disposed between cutter blades 174 and finger plates 156, 158, or 160.

Employment of a plurality of movable finger plates (e.g., 156, 158, and 160) allows the reducing action of second grinder 34 to be effectively multiplied by the numeric quantity of finger plates; the exemplary embodiment discussed herein, by a factor of three. Additionally, the probability of an excess amount of material simultaneously binding all three of finger plates 156, 158, and 160 as material moves from inlet 164 to outlet 166 is decreased substantially as the number of finger plates is increased. Thus, the plurality of movable finger plates permits grinder 34 to reliably reduce the waste material to a more finely divided state.

FIGS. 10 and 11 illustrate autoclave 43. Autoclave 43 is a pressure vessel including a shell 338, an inlet opening 44 closeable and sealable by an inlet door assembly 200, a discharge opening 60 closeable and sealable by a discharge door 252, a plurality of steam inlets 310, and a rotatable auger assembly 332. Finely divided contaminated waste material is placed within shell 338 through opening 44, after which an inlet door 202 of door assembly 202 is secured in a closed position. Rotation of auger 332 is then initiated, and maintained while steam is allowed to enter shell 338 through steam inlet ports 310.

Shell 338 is generally cylindrical in shape, and includes a first end 54 and a second end 56, both ends closed by members (shown as dished tank heads) welded or otherwise seemingly affixed to the cylindrical sidewall of shell 338.

Auger assembly 332 includes shaft 46, a first helical auger 48, and a second helical auger 50. First auger 48 and second auger 50 are both configured in two portions of approximately equal lengths, each portion having an opposite hand of rotation; i.e., the first portion of augers 48, 50 is provided a positive helix angle and the second portion is provided a negative helix angle. Second auger 50 is of a relatively small outside diameter and has an inside diameter suitable for being slipped over shaft 46 and welded to shaft 46. First auger 48 is of a much larger outer diameter, and is configured to have a slip fit within shell 338 so that it may serve to scrape the inner wall surfaces of shell 338. An inner diameter of first auger 48 is substantially larger than is the outer diameter of second auger 50, so that a large radial gap exists between the two. First auger 48 is affixed to shaft 46 by a series of rigid spokes 334. A first auger 48 portion having one hand of rotation is affixed to a first end 46a of shaft 46 surrounding a first portion of inner auger 50 having an opposite hand of rotation affixed to first end 46a of shaft 46. Second portions of first auger 48 and second auger 50 having opposite ends of rotation are secured to a second end 46b of shaft 46. As a result, rotation of auger assembly 332 in a first direction causes waste material particles to be circulated from a longitudinal center of autoclave 43 towards first and second ends 54, 56 in the region of the inner periphery of shell 338 and inwardly toward the longitudinal center in regions away from the inner periphery of shell 338. In a cross-sectional view, the waste material therefore is constantly agitated and tumbled while being circulated. Rotation of auger assembly 332 in the opposite direction of rotation causes a similar circulation of material in a cross-sectional view, but in opposite directions of circulation. In either case, all surfaces of each particle are exposed for approximately equal lengths of time to steam within autoclave 43.

In operation, reduced waste material is transferred from second conveyor 40 through inlet opening 44 into autoclave 43. Upper door assembly 200 includes a movable door 202 and a fluid cylinder 204 used for selectively moving door 200 between an open position for loading waste material into autoclave 43 and a closed, sealing position for sterilizing material within autoclave 43. Upper door assembly 202 also includes a limit switch (not shown) for sending a "door open" or "door closed" signal to the PLC. Before closing door 200, inlet opening 44 is rinsed with disinfectant spray to wash any waste material in the region of opening 44 into shell 338 before closing of door 200 and to disinfect adjacent exterior surfaces of shell 338 and of door assembly 202 which may have been in contact with contaminated waste material.

Similarly, a lower door assembly 252 is provided for transferring sterilized waste material from autoclave 43 to third conveyor 62.

Third conveyor 62 is shown in FIGS. 1, 10, and 12. Reduced and sterilized waste material falls by gravity through outlet opening 60 of autoclave 43, when outlet door assembly 252 is opened, onto a horizontally disposed portion 344 of conveyor 62. Conveyor 62 is a belt-type conveyor, provided with extending members 342 for lifting the reduced sterilized material in a vertically disposed portion of third conveyor 62. It is also contemplated that a screw-type conveyor can be used although the screw type conveyor may be shaftless. The sanitized medical waste material particles fall by gravity from members 342 onto a discharge chute 340. Chute 340 is extended through an opening in a sidewall 70 of containment chamber housing 74 to a container (not shown) suitable for hauling the sterilized, reduced medical waste material to a landfill or other final disposal site.

While the embodiments illustrated in the FIGS. and described above are presently preferred, it should be understood that these embodiments are offered by way of example only. The present invention is not intended to be limited to any particular embodiment, but is intended to extend to various modifications that nevertheless fall within the scope of the appended claims. For example, it is also contemplated that other types of grinding or size reducing apparatus (e.g., a hammer mill) may be employed. An autoclave may be inclined in an elevation view, so that a second end is higher than a first end. Another type of material feeder (e.g., screw) may be substituted for a delta feeder. It is also contemplated that the steam generation plant be supplemented by an external, to the containment chamber, generation plant, such as the hospital's steam generation plant. It is also contemplated that the medical waste disposal system be provided with a motive assembly such as an engine and drive wheels, to selectively move the entire system. Other modifications will be evident to those of ordinary skill in the art, will be viewed as matters of construction rather than invention.

What is claimed is:

1. A grinder assembly in a medical waste disposal plant, said grinder assembly comprising:
    a grinding housing having opposed, parallel sides defining a grinding chamber with said grinding housing having an inlet and an outlet in communication with the grinding chamber and said path of medical waste,
    a cutter assembly disposed in the grinding chamber, said cutter assembly comprising:
    a shaft rotatably mounted to the sides of the grinding housing and connected to a means for rotation, and
    a plurality of first cutter blades mounted on the shaft at axially spaced apart intervals and extending radially beyond a plurality of second cutter blades mounted on the shaft at spaced apart intervals between said first cutter blades, and,
    a movable finger plate rotatably mounted to the sides of the grinding housing in the grinding chamber and positioned to allow the first and second cutter blades to move between a plurality of slots in the finger plate, said finger plate connected to a means for movement towards and away from said first and second cutter blades and a transponder responsive to selected forces on the finger plate.

2. The grinder assembly of claim 1 wherein the means for rotation is a motor and a transmission operable to set selected speeds of rotation of the shaft.

3. The grinder assembly of claim 2 wherein the speeds of rotation are set with a programmable logic controller.

4. The grinder assembly of claim 1 wherein the means for movement is a fluid cylinder assembly in fluid communication with a fluid pump.

5. The grinder assembly of claim 1 wherein the forces and corresponding response of the means for movement are set with a programmable logic controller.

6. The grinder assembly of claim 1 including at least one additional movable finger plate mounted in the grinding chamber.

7. A medical waste disposal system for loading, reducing and sterilizing medical waste, said medical waste disposal system comprising:
    a means for transporting the medical waste disposal system;
    a means for loading medical waste into the medical waste disposal system,
    a means for grinding medical waste into a reduced volume of medical waste in communication with the means for loading, a means for sterilizing medical waste in the medical waste disposal system, and a means for conveying medical waste through the medical waste disposal system between the means for grinding and the means for sterilizing.

8. The medical waste disposal system of claim 7 wherein the means for transporting is a wheeled trailer including a containment chamber configured to enclose the medical waste disposal system, with said containment chamber having an exterior hopper to receive medical waste and an outlet to convey the reduced, sterilized medical waste to a disposal container.

9. The medical waste disposal system of claim 7 wherein the means for grinding is a rotating shaft with a plurality of spaced blades mounted thereon, said shaft mounted in a grinding chamber with at least one movable finger plate mounted in said grinding chamber and positioned to allow the blades to move between the fingers of said plate, said movable finger plate further connected to a fluid cylinder to move the finger plate towards and away from the blades.

10. The medical waste disposal system of claim 7 wherein the means for conveying is a plurality of conveyors configured to move the medical waste from the means for loading to the means for grinding and from the means for grinding to the means for sterilizing and from the means for sterilizing to the disposal container.

11. The medical waste disposal system of claim 10 wherein the conveyors are selected from a group comprising: a belt and a screw.

12. The medical waste disposal system of claim 7 wherein the means for sterilizing is an autoclave in communication with the means for conveying and a steam generation plant.

13. The medical waste disposal system of claim 12 wherein the autoclave is mounted in one of a horizontal and an inclined aspect with respect to the means for transporting.

14. The medical waste disposal system of claim 13 wherein the autoclave includes a pair of screw blades having opposed pitches mounted inside the autoclave and configured to mix and move the medical waste contained inside the said autoclave.

15. The medical waste disposal system of claim 12 wherein the steam generation plant is in communication with a plurality of steam inlets mounted within the autoclave and the means for transporting.

* * * * *